(12) United States Patent
Wang (10) Patent No.: US 9,629,678 B2
(45) Date of Patent: Apr. 25, 2017

(54) CONTROLLED IRRIGATED CATHETER ABLATION SYSTEMS AND METHODS THEREOF

(75) Inventor: Huisun Wang, Maple Grove, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1612 days.

(21) Appl. No.: 12/345,975

(22) Filed: Dec. 30, 2008

(65) Prior Publication Data

US 2010/0168736 A1 Jul. 1, 2010

(51) Int. Cl.
*A61B 18/14* (2006.01)
*A61B 17/00* (2006.01)
*A61B 18/00* (2006.01)

(52) U.S. Cl.
CPC ..... *A61B 18/1492* (2013.01); *A61B 2017/00084* (2013.01); *A61B 2018/00029* (2013.01); *A61B 2218/002* (2013.01)

(58) Field of Classification Search
USPC .......... 604/22, 507, 510; 606/41, 49, 50, 51, 606/31; 607/119
See application file for complete search history.

(56) References Cited

U.S. PATENT DOCUMENTS

| | | | |
|---|---|---|---|
| 5,056,517 A | | 10/1991 | Fenici |
| 5,160,194 A | * | 11/1992 | Feldman ............ 362/109 |
| 5,230,349 A | | 7/1993 | Langberg |
| 5,304,214 A | * | 4/1994 | DeFord et al. ............ 607/105 |
| 5,348,554 A | | 9/1994 | Imran et al. |
| 5,423,811 A | | 6/1995 | Imran et al. |
| 5,462,521 A | | 10/1995 | Brucker et al. |
| 5,545,161 A | | 8/1996 | Imran |
| 5,643,197 A | | 7/1997 | Brucker et al. |

(Continued)

FOREIGN PATENT DOCUMENTS

| | | |
|---|---|---|
| WO | 99/35986 A1 | 7/1999 |
| WO | 03/024349 | 3/2003 |

(Continued)

OTHER PUBLICATIONS

Wong et al. "Effect of Saline Irrigation Flow Rate on Temperature Probe during Cooled Radiofrequency Ablation." Journal of Interventional Cardiac Electrophysiology 4, 321-326(2000).*

(Continued)

*Primary Examiner* — Scott Medway
(74) *Attorney, Agent, or Firm* — Dykema Gossett PLLC (57) ABSTRACT

The present invention relates to open irrigated catheter ablation systems and methods used in connection with open irrigated catheter systems. The systems and related methods can control irrigation fluid flow to obtain temperature responses indicative of temperatures associated with an ablation procedure. Embodiments of the present invention provide irrigated catheter ablation systems having controlled irrigation fluid flow that can be directed at target areas where coagulation is more likely to occur to help minimize blood coagulation and associated problems. The irrigated fluid flow may be regulated in connection with an established or predetermined temperature threshold to improve or better optimize cooling and ablation properties of the system. In embodiments, irrigation flow may be either delayed or intermitted.

23 Claims, 6 Drawing Sheets

(56) References Cited

U.S. PATENT DOCUMENTS

| | | | |
|---|---|---|---|
| 5,662,680 A * | 9/1997 | Desai | 606/210 |
| 5,792,140 A | 8/1998 | Tu et al. | |
| 5,843,152 A | 12/1998 | Tu et al. | |
| 5,860,951 A * | 1/1999 | Eggers et al. | 604/510 |
| 5,913,856 A | 6/1999 | Chia et al. | |
| 6,017,338 A | 1/2000 | Brucker et al. | |
| 6,056,745 A * | 5/2000 | Panescu et al. | 606/42 |
| 6,210,406 B1 * | 4/2001 | Webster | 606/41 |
| 6,287,304 B1 * | 9/2001 | Eggers et al. | 606/37 |
| 6,336,926 B1 * | 1/2002 | Goble | 606/34 |
| 6,391,028 B1 * | 5/2002 | Fanton et al. | 606/45 |
| 6,405,078 B1 * | 6/2002 | Moaddeb et al. | 604/21 |
| 6,406,476 B1 * | 6/2002 | Kirwan et al. | 606/50 |
| 6,579,288 B1 * | 6/2003 | Swanson et al. | 606/41 |
| 6,602,242 B1 | 8/2003 | Fung et al. | |
| 6,611,699 B2 | 8/2003 | Messing | |
| 6,666,862 B2 * | 12/2003 | Jain et al. | 606/41 |
| 6,702,811 B2 * | 3/2004 | Stewart et al. | 606/41 |
| 6,827,715 B2 * | 12/2004 | Francischelli et al. | 606/34 |
| 6,837,886 B2 * | 1/2005 | Collins et al. | 606/41 |
| 6,849,075 B2 * | 2/2005 | Bertolero et al. | 606/41 |
| 7,077,841 B2 * | 7/2006 | Gaiser et al. | 606/41 |
| 7,097,644 B2 * | 8/2006 | Long | 606/41 |
| 7,127,770 B2 * | 10/2006 | Clegg et al. | 15/105 |
| 7,166,105 B2 | 1/2007 | Mulier et al. | |
| 7,285,116 B2 * | 10/2007 | de la Rama et al. | 606/27 |
| 7,542,807 B2 * | 6/2009 | Bertolero et al. | 607/119 |
| 7,708,733 B2 * | 5/2010 | Sanders et al. | 606/41 |
| 7,811,282 B2 * | 10/2010 | McClurken | 606/49 |
| 2005/0222564 A1 | 10/2005 | Plaza | |
| 2005/0273090 A1 * | 12/2005 | Nieman et al. | 606/15 |
| 2006/0041254 A1 * | 2/2006 | Francischelli et al. | 606/41 |
| 2006/0116675 A1 * | 6/2006 | McClurken et al. | 606/51 |
| 2006/0200049 A1 * | 9/2006 | Leo et al. | 600/587 |
| 2007/0156131 A1 | 7/2007 | Datta | |
| 2007/0270791 A1 * | 11/2007 | Wang et al. | 606/41 |
| 2007/0287933 A1 * | 12/2007 | Phan et al. | 600/566 |
| 2008/0082145 A1 | 4/2008 | Skwarek | |
| 2008/0161795 A1 | 7/2008 | Wang | |
| 2009/0312756 A1 * | 12/2009 | Schlesinger et al. | 606/41 |

FOREIGN PATENT DOCUMENTS

| | | |
|---|---|---|
| WO | 03/024349 A1 | 3/2003 |
| WO | 2005/048858 A1 | 6/2005 |

OTHER PUBLICATIONS

Wittkampf, et al., Radiofrequency Ablation with a Cooled Porous Electrode Catheter, JACC vol. 11, No. 2, Feb. 1988: 17A Abstracts.

Wittkampf, et al., Saline-Irrigated Radiofrequency Ablation Electrode with External Cooling, Journal of Cardiovascular Electrophysiology, vol. 16, No. 3, Mar. 2005.

Author: Wittkampf, Fred H., Title: Radiofrequency ablation with a cooled porous electrode catheter, Citation: JACC vol. II, No. 2; 17a, Publication Date: Feb. 1988.

Author: Wittkampf, Fred, Title: Saline-Irrigated Radiofrequency ablation electrode with external cooling, Citation: Journal of Cardiovascular Electrophysiology, vol. 16, No. 3, Publication date: Mar. 2005.

Author: Wong, Wai Shun, Title: Effect of Saline Irrigation Flow Rate on Temperature Profile during Cooled Radiofrequency Ablation, Citation: Journal of Interventional Cardiac Electrophysiology 4, 321-326(2000), © Kluwer Academic Publishers. Manufactured in The Netherlands, Reference pp. 6. Publication Date: 2000.

European Search Report—EP 14157953.2, May 2, 2014.

* cited by examiner

CONTROLLED IRRIGATED CATHETER ABLATION SYSTEMS AND METHODS THEREOF

BACKGROUND OF THE INVENTION a. Field of the Invention

The present invention relates to irrigated catheter assembly systems and methods for ablating tissue using controlled irrigation flow. The present invention further relates to open irrigated catheter ablation systems having irrigation fluid flow that may be regulated in connection with a predetermined temperature threshold.

b. Background Art

Electrophysiology catheters are used for an ever-increasing number of procedures. For example, catheters are used for diagnostic, therapeutic, and ablative procedures, to name just a few procedures. Typically, a catheter is manipulated through the patient's vasculature to an intended site, for example, a site within the patient's heart. The catheter commonly carries one or more electrodes, which may be used for ablation, diagnosis, and/or other treatments.

There are a number of methods used for ablation of desired areas, including for example, radiofrequency (RF) ablation. RF ablation is accomplished by transmission of radiofrequency energy to a desired target area through an electrode assembly to ablate tissue at a target site. Because RF ablation may generate significant heat, which if not controlled could result in tissue damage, such as steam pop, tissue charring, and the like, it is often desirable to include a mechanism to irrigate the target area and the device with biocompatible fluids, such as saline solution. The use of fluid irrigated ablation catheters can also prevent the formation of soft thrombus and/or blood coagulation.

Generally, there are two classes of irrigated electrode catheters, open and closed irrigation catheters. Closed ablation catheters can circulate a cooling fluid within the inner cavity of the ablation electrode. Open ablation catheters can deliver the cooling fluid through open outlets or openings on the surface of the electrode. Open ablation catheters use the inner cavity of the electrode, or distal member, as a manifold to distribute saline solution (or other irrigation fluids known to those skilled in the art) to one or more passageways that lead to openings/outlets provided on the surface of the electrode. The saline thus flows directly through the outlets of the passageways onto or about the distal electrode member. This direct flow through the distal electrode tip lowers the temperature of the distal tip during operation, which may make accurate monitoring and control of the ablation process somewhat more challenging.

While open irrigated ablation catheters may improve the safety of RF catheter ablation by preventing protein aggregation and blood coagulation through the dissipation of heat by providing fluid to the site during the ablation procedure, direct contacting fluid irrigation has the tendency to cool the electrode temperature dramatically during ablation procedures. The irrigation fluid flow ultimately cuts off the electrode temperature from rising, which may result in increased (and possibly more than desirable) ablation in a target area. As such, it can be desirable to control and more accurately monitor the temperature of an electrode performing ablation.

BRIEF SUMMARY OF THE INVENTION

The present invention is directed to improved open irrigated catheter ablation systems and methods used in connection with open irrigated catheter systems. Among other things, systems and related methods are provided that can control irrigation fluid flow and obtain an effective temperature response with respect to an ablation procedure. Embodiments of the present invention provide an irrigated catheter ablation system having controlled irrigation fluid flow directed at target areas, for example, where coagulation is more likely to occur so as to minimize blood coagulation and associated problems. The irrigated fluid flow may be regulated in connection with a predetermined temperature threshold to improve or better optimize cooling and ablation properties associated with the system.

The present invention provides an ablation system having an open irrigated ablation electrode coupled to or connected with a catheter shaft forming an open irrigated catheter assembly in connection with a fluid source, an energy source, and a temperature control mechanism for regulating irrigation fluid flow within the catheter shaft assembly.

The present invention further discloses an ablation system having an open irrigated ablation catheter assembly including an open irrigated ablation electrode coupled to or connected to a catheter shaft forming the open irrigated catheter assembly in connection with a fluid source, an energy source, such as, for example, radio frequency (RF) generator, and a processor for regulating the temperature control of the electrode performing the ablation.

The present invention provides a method of controlling the irrigation of biological tissue. The method includes the steps of providing an irrigated catheter ablation system including an irrigated ablation catheter assembly, a fluid source connected to the catheter assembly, an energy source connected to the catheter assembly; and an irrigation temperature control mechanism in communication with the fluid source and energy source; presetting a temperature threshold for the system that regulates irrigation fluid flow from the passageway of the catheter assembly; positioning the irrigated electrode of the irrigated ablation catheter assembly at a target location; applying energy from the energy source to the target location through the irrigated electrode; collecting temperature measurements from a thermal sensor disposed within the irrigated electrode; irrigating the ablation electrode forming an irrigation flow through the passageway of the electrode; and completing the application of energy to the target location to form an ablation lesion.

The invention further contemplates alternate methods for irrigating biological tissue, including a delayed irrigation method and an intermitted irrigation method. The delayed irrigation method involves collecting temperature measurements of the open irrigation electrode until the collected temperature measurements of the electrode reach a predetermined upper temperature threshold. Once the upper temperature threshold is met, the irrigation fluid flow from the passageways of the open irrigation electrode increases from a maintenance flow rate to an amplified irrigation flow rate. The increased irrigation flow continues until the ablation is completed. In comparison, during the intermitted irrigation method, once the irrigation fluid flow from the passageways of the open irrigation electrode is increased, the intermitted method further includes collecting temperature measurements of the electrode until the temperature measurements of the electrode reach a predetermined lower temperature threshold. Once the electrode temperature measurements reach the lower threshold level, the irrigation flow is reduced to the maintenance flow level through the passageway of the electrode. Once the irrigation flow is reduced, temperature measurements continue to be collected from a thermal sensor disposed within the irrigated electrode until the temperature measurements once again return to the predetermined upper temperature threshold. The irrigation fluid flow is then increased again through the passageway of the electrode therein creating an intermitted irrigation cycle. Accordingly, the irrigation flow is reduced periodically during the intermitted irrigation cycle in response to the temperature. The intermitted irrigation cycle is continued until the ablation is complete. The intermitted irrigation method further provides that the irrigation may be turned off periodically during the ablation procedure to check the temperature response of the electrode until the ablation is completed.

The foregoing and other aspects, features, details, utilities, and advantages of the present invention will be apparent from reading the following description and claims, and from reviewing the accompanying drawings.

DETAILED DESCRIPTION OF THE INVENTION

In general, the instant invention relates to irrigated catheter ablation systems and to methods of using irrigated catheter ablation systems. For purposes of this description, similar aspects among the various embodiments described herein will generally be referred to by the same reference number. As will be appreciated, however, the structure of the various aspects may differ among various embodiments.

Figure 1:
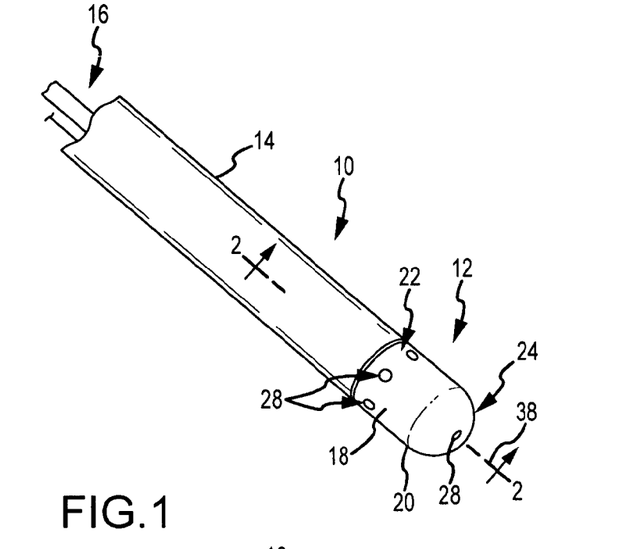
FIG. 1 is an isometric view of an ablation electrode according to an embodiment of the present invention.
Figure 2:
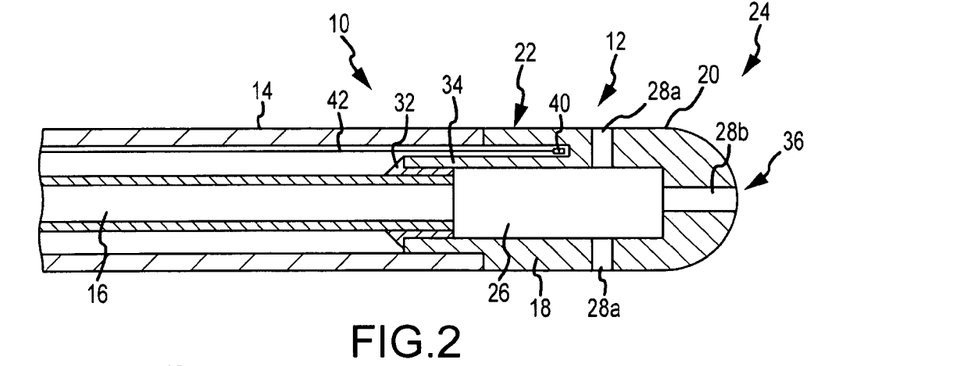
FIG. 2 is a cross-sectional view of an ablation electrode of the type generally shown in FIG. 1.
Figure 3:
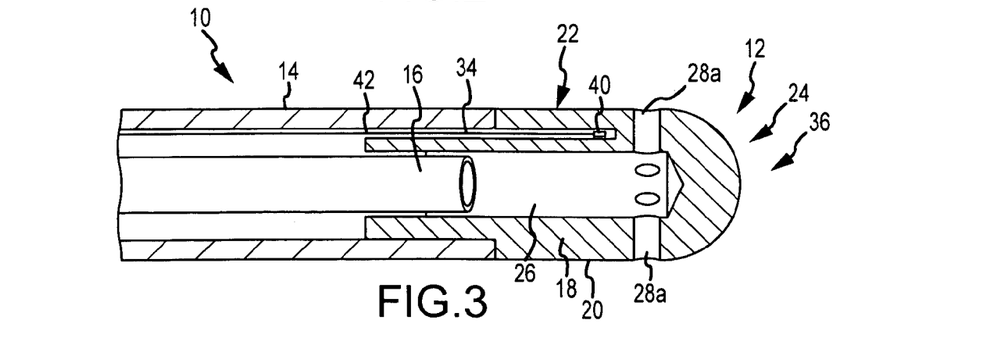
FIG. 3 is a cross-sectional view of an ablation electrode according to another embodiment of the present invention.

Open irrigated catheter ablation systems of the present invention include an irrigated ablation catheter assembly 10, as generally shown in FIG. 1. The illustrated irrigated ablation catheter assembly 10 includes an ablation electrode 12. While embodiments of the invention disclosed herein may describe RF ablation catheter assemblies and related systems, the invention is not so limited, and the invention may include or involve other types of ablation electrodes and assemblies in which the temperature of the device and a targeted tissue area may be factors during the procedure. FIGS. 2 and 3, discussed in further detail below, illustrate specific open irrigated ablation electrodes 10 according to alternate embodiments associated with the present invention. Moreover, FIGS. 4 and 5, discussed in further detail below, illustrate catheter ablation systems embodying features associated with the present invention.

Embodiments of open irrigated catheter ablation systems in accordance with the present invention include an open irrigated catheter assembly 10 having an open irrigated electrode 12 configured to control the flow of irrigation fluid to an ablation site. The present invention encompasses irrigated catheter assembly systems that control and regulate the irrigation fluid flow to an ablation site, for example, to improve or optimized ablation on a tissue while irrigating the surface of the tissue. The system may be configured and/or regulated to provide either intermitted irrigation fluid flow throughout the ablation procedure or a delayed onset of irrigation to ensure good physical contact of electrode 12 with the ablation site. In embodiments, temperature feedback may be used in combination with responsive irrigation flow to improve or optimize tissue ablation when using convention open irrigated ablation catheters to perform an ablation procedure or technique on biological tissue. Such conventional irrigation catheters include, but are not limited to, those such as IBI Therapy™ Cool Path™ Ablation Catheter available from Irvine Biomedical, Inc.

In particular, one embodiment of the present invention provides a system and related method for performing RF ablation that includes the delayed onset of the irrigation fluid flow to electrode 12. The onset of therapeutic irrigation fluid flow may be controllably delayed until electrode 12 reaches a predetermined temperature threshold, such as, without limitation, about 65 degrees Celsius. With such embodiments, after electrode 12 reaches the temperature threshold level, the irrigation fluid flow can be started to provide cooling to the electrode. The delayed onset of the irrigation flow better ensures that an accurate temperature reading of the electrode may be obtained during the initial ablation procedure, which further helps ensure improved physical contact between electrode 12 and a targeted site (e.g., targeted tissue). On the other hand, if the temperature threshold is not met upon the application of the ablation energy or shortly thereafter, electrode 12 may need to be repositioned to ensure sufficient or proper physical contact with targeted tissue. Since the temperature threshold is generally set below an associated safety limit, e.g., about 65 degrees C., heat related coagulum that is present can be eliminated in connection with the ablation.

An alternate embodiment of the present invention provides a system and related method for performing ablation, such as RF ablation, that includes intermitted fluid irrigation flow such that irrigation fluid may be regulated (i.e., increased and decreased) in response to the temperature of electrode 12. More particularly, the intermitted fluid irrigation flow may be controlled by a predetermined temperature threshold, such as, for example, about 65 degrees. Accordingly, the irrigation fluid flow may be increased when the electrodes reaches about 65 degrees and is then decreased once a reduced temperature threshold is reached, such as, for example about 40 degrees. The irrigation fluid flow may be provided for a fixed intermitted duration (i.e., for example, a fixed period of time), a variable intermitted duration that is based solely on temperature threshold levels, or some combination of the foregoing.

As noted, open irrigated catheter assemblies may be used for a variety of treatments and procedures. FIG. 1 is an isometric view of part of an embodiment of an irrigated ablation catheter assembly 10. The irrigated ablation catheter assembly 10 includes an open irrigated ablation electrode 12 connected to a catheter shaft 14 having at least one fluid delivery tube 16 therein. The ablation electrode 12 includes an outer body portion 18 having an outer surface 20, and includes a proximal portion 22 and a distal portion 24. As further illustrated in FIGS. 2 and 3, electrode 12 of the catheter assembly 10 may further include an inner cavity 26 that may be coupled to or is in fluid communication with fluid delivery tube 16. The open irrigated electrode 12 further includes at least one fluid or irrigation passageway 28 that extends from inner cavity 26 to outer surface 20 of electrode 12.

Electrode 12 may be comprised of any electrically, and potentially thermally, conductive material known to those of ordinary skill in the art for delivery of ablative energy to target tissue areas. Examples of electrically conductive materials include gold, platinum, iridium, palladium, stainless steel, and mixtures thereof. A portion of electrode 12 may be configured to connect to (or be received by) catheter shaft 14 of catheter assembly 10 therein coupling electrode 12 to form an embodiment of a catheter assembly 10. It is noted that alternate configurations may be employed with other embodiments in which an electrode may be comprised of multiple members that connect or fit together to form the electrode. Various materials may be used in the formation of such electrodes, including a combination of electrically conductive materials and materials that are less thermally conductive.

In the illustrated embodiment, outer body portion 18 of electrode 20, which includes outer surface 20, is generally cylindrical in shape and terminates in a hemispherical end. However, outer body portion 18 may be provided in alternate configurations that may be directed to the design of the catheter assembly and/or the procedures being performed. Proximal portion 22 of electrode 12 is generally adjacent to catheter shaft 14, and may be disposed on the distal end of catheter shaft 14. Distal portion 24 of electrode 12 is generally more remote from catheter shaft 14 and includes the portion of electrode 12 intended to come into operative contact with tissue. Distal portion 24 further includes a distal end 36 which may be generally hemispherical, although other shapes and configurations are also contemplated by the present invention.

Proximal portion 22 of electrode 12 may further include a mounting portion, such as mounting shaft 34 that is provided on or in connection with the proximal end 30 of electrode 12. Mounting shaft 34 may be connected to or an integral part of proximal end 30 of proximal portion 22 of electrode 12 and may be received within or otherwise connected to catheter shaft 14 of assembly 12. In an embodiment, coupling member 32 is disposed between mounting shaft 34 and catheter shaft 14. A coupling member 32, such as a seal or adhesive, is provided to ensure that electrode 12 is connected to catheter shaft 14. Coupling member 32 is generally known in the art and includes any type of material known for such a purpose to those of ordinary skill in the art. Moreover, coupling member 32 may have alternate configurations or arrangements to connect electrode 12 with catheter shaft 14.

Electrode 12 may further include a temperature or thermal sensor 40 (generally represented in FIGS. 2 and 3) positioned within distal portion 24 of electrode 12. Thermal sensor 40 may be configured and positioned to provide improved or optimized accurate temperature sensing by electrode 12 as ablative energy is applied by catheter assembly 10. A lead wire 42 may be coupled to thermal sensor 40 and may extend along the catheter assembly 12 such that the temperature of electrode 12 may be communicated to a processor or controller within the catheter assembly system to help control overall system operation and regulation of the irrigation fluid flow and ablation performed by the catheter assembly system. The configuration of thermal sensor 40 may be modified to work with various designs of open irrigation catheter assemblies. Moreover, more than one thermal sensor 40 may be provided in connection with an electrode. In embodiments in which a plurality of sensors 40 are provided, the sensors may be used in combination to provide temperature readings associated with an electrode 12.

With reference to FIGS. 2 and 3, inner cavity 26 of electrode 12 includes a central longitudinal axis 38 that extends along the length of electrode 12. Inner cavity 26 may have a generally tubular configuration, although alternate embodiments of the inner cavity are also contemplated. In the illustrated embodiment, inner cavity 26 extends through proximal portion 22 and into distal portion 24 of electrode 12.

As shown in FIGS. 2 and 3, an open irrigation electrode 12 includes at least one fluid passageway 28—such as, without limitation, passageways 28a and/or 28b shown in FIG. 2). Such passageway(s) 28 may include and be referred to as conduit(s), irrigation port(s), irrigation hole(s), channel (s), or other types of structures employed by those of skill in the art. In general, passageway 28 extends from internal cavity 26 to an outer surface 20 of electrode 12. Moreover, some open irrigation electrodes, such as those illustrated in FIGS. 2 and 3, may include at least one passageway 28a that is perpendicular, or substantially perpendicular, to the central longitudinal axis 38 of electrode 12. In addition, as generally shown in FIG. 2, passageway 28b may be provided that extends along central longitudinal axis 38 from inner cavity 26 to distal end 36 to provide irrigation at distal portion 24 of electrode 12.

In addition to those configurations reflected in FIGS. 2 and 3, various alternative embodiments of fluid passageways may be incorporated within electrode 12, such as those described in currently pending applications assigned U.S. patent application Ser. Nos. 11/939,195 and 11/939,206, both of which are herein fully incorporated by reference. Furthermore, passageways 28 are disposed circumferentially around electrode 12. In embodiments, the passageways may be provided so that they are generally equidistant from one another, although alternate configurations and placements of passageway 28 may be used depending on the design or desired performance (e.g., to cover a given volume of fluid flow) of electrode 12.

Accordingly, the design of the passageways 28 may be modified to obtain a desired flow rate of the irrigation fluid based on a temperature threshold set by the overall system. The size and configuration of passageway 28 (such as 28a and/or 28b) may be varied depending on the size and design of an associated electrode 12. In an embodiment, the diameter of passageway 28 may range from 10-20 thousandths of an inch. In another embodiment, the diameter of the passageway 28 may range from 12-16 thousandths of an inch. Moreover, the flow rate and/or volume of fluid flow may range from 13-20 ml/min. The diameter size of passageway 28 may be configured to permit a given flow volume or rate, and further may be varied in connection with the number of passageways provided by electrode 12, as well as the length of the electrode, or with other features associated with the electrode or catheter assemblies.

In addition to various passageway networks and configurations, electrode 12 may include additional components, such as those typically used by ablation electrodes, including but not limited to pressure sensors, power wires, or other features or components traditionally integrated with catheter assemblies.

Figure 4:
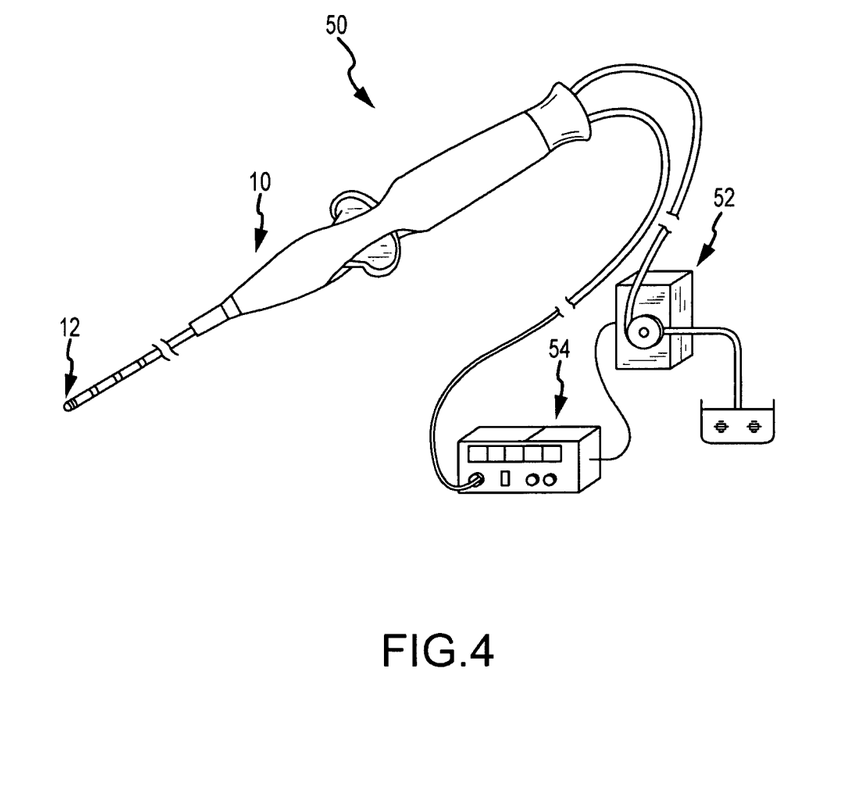
FIG. 4 is an isometric view of an ablation catheter system according to an embodiment of the present invention, the illustrated system including an irrigated catheter assembly operably connected to an energy source and a fluid source.
Figure 5:
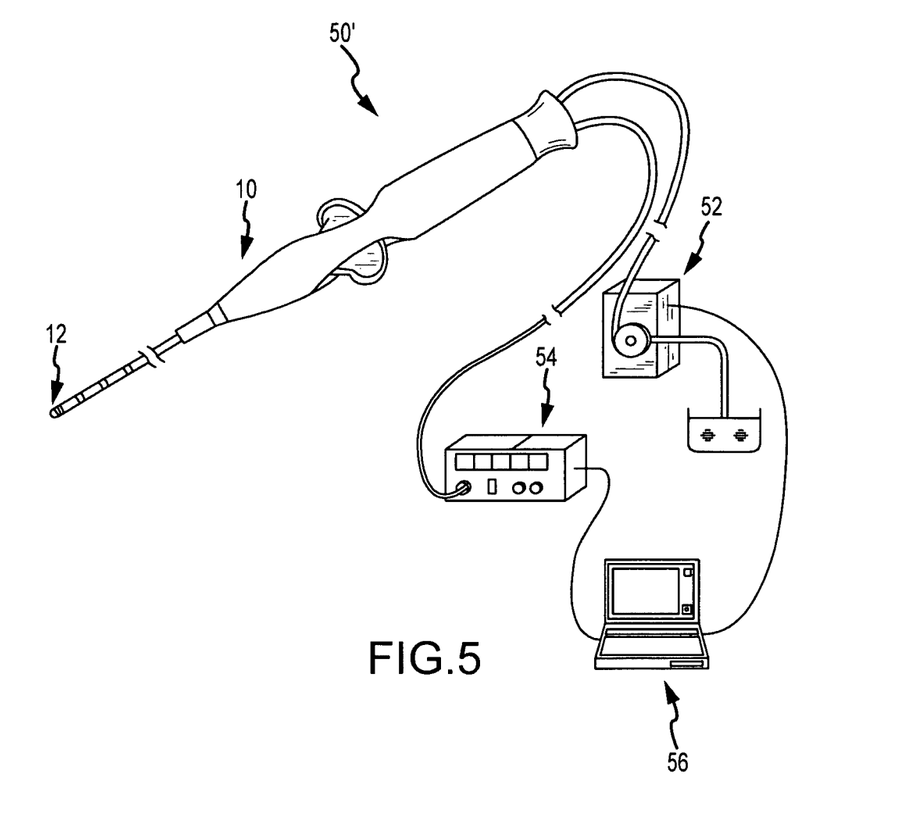
FIG. 5 is an isometric view of an ablation catheter system according to another embodiment of the present invention, the illustrated system including an irrigated catheter assembly operably connected to an energy source, a fluid source, and a processor.

An open irrigation catheter assembly 12, such as generally described above, may be integrated into alternate embodiments of catheter assembly system 50s, for example, as shown in FIGS. 4 and 5. System 50, 50' may be configured to control and regulate the flow of irrigation fluid such that the relative positioning of the electrode and establishment of sufficient or improved physical contact is, at least in part, facilitated by a temperature feedback provided by electrode 12.

As generally shown in the embodiment illustrated in FIG. 4, catheter assembly 10 may be operably connected to a fluid source 52 (e.g., a pump assembly) and an energy source 54 (e.g., an RF generator assembly), together comprising an embodiment of a catheter system 50. The fluid source 52 and energy source 54 may serve to facilitate operation of ablation procedures and may involve monitoring any number of chosen variables (e.g., temperature of ablation electrode, ablation energy, and/or position of the assembly), assisting in manipulation of the assembly during the use, and providing the requisite energy from a source that is delivered to the electrode 12. Furthermore, additional components may be integrated into the system. By way of example, without limitation, such additional components may include visualization, mapping and navigation components known in the art, including St. Jude Medical, Inc.'s NavX® system or other related systems.

As generally represented in FIG. 4, fluid source 52 and energy source 54 may be provided in combination with a catheter assembly 10 to comprise a system 50. Fluid source 52 can comprise various known fluid sources, including fixed volume rolling pumps, variable volume syringe pumps, and various other pump assemblies known to those skilled in the art. Moreover, the fluid provided by fluid source 52, may comprise a suitable biocompatible fluid, such as saline. The energy source 54 may comprise, for example and without limitation, an IBI-1500T RF Cardiac Ablation Generator available from Irvine Biomedical, Inc. The energy source can also comprise various other known energy sources. In order to obtain controlled/regulated fluid flow within the system, energy source 54 may also, if desired, be configured with a temperature threshold setting and pump control switch (not shown). In an embodiment, energy source 54 (i.e., generator) may monitor and detect the temperature of electrode 12 of catheter assembly 10 and, once an established temperature threshold is met, activate fluid source 52, therein either increasing/decreasing fluid flow or turning the pump completely on or off. Accordingly, FIG. 4 generally illustrates a system having a closed control loop to control the flow of irrigation fluid, e.g., saline, based on the temperature feedback provided by catheter assembly 10.

FIG. 5 generally illustrates another embodiment of the invention wherein system 50' integrates a controller 56, such as, for example, a computer or other type of processor or signal control device. Controller 56 may be configured to receive input from energy source 54. Input received by controller 56 may further include temperature readings obtained from catheter assembly 10 (such as those provided in connection with a thermal sensor 40 of electrode 12). Controller 56 can process temperature readings and make comparisons/calculations with respect to specified temperature threshold levels. Once a desired temperature threshold levels is established or obtained, controller 56 can output a signal to pump 52, which can in turn control irrigation fluid flow supplied to catheter assembly 12. Continued (periodic or continuous) temperature readings from catheter assembly 10 may be provided to controller 56 and based on changes in the temperature readings of catheter assembly 10, controller 56 may modify its signal (e.g., instructions) to pump 52, which can increase or decrease the associated fluid flow. Various data, such as, for example, irrigation fluid flow (cc/min), temperature measurements, duration of fluid flow, and electrode temperature response may be processed by controller 56. In an embodiment, controller 56 may also help assess (e.g., chart) various data or parameters, which may be reviewed by a user. Moreover, the system 50 can provide for dynamic assessment and review.

Figure 6:
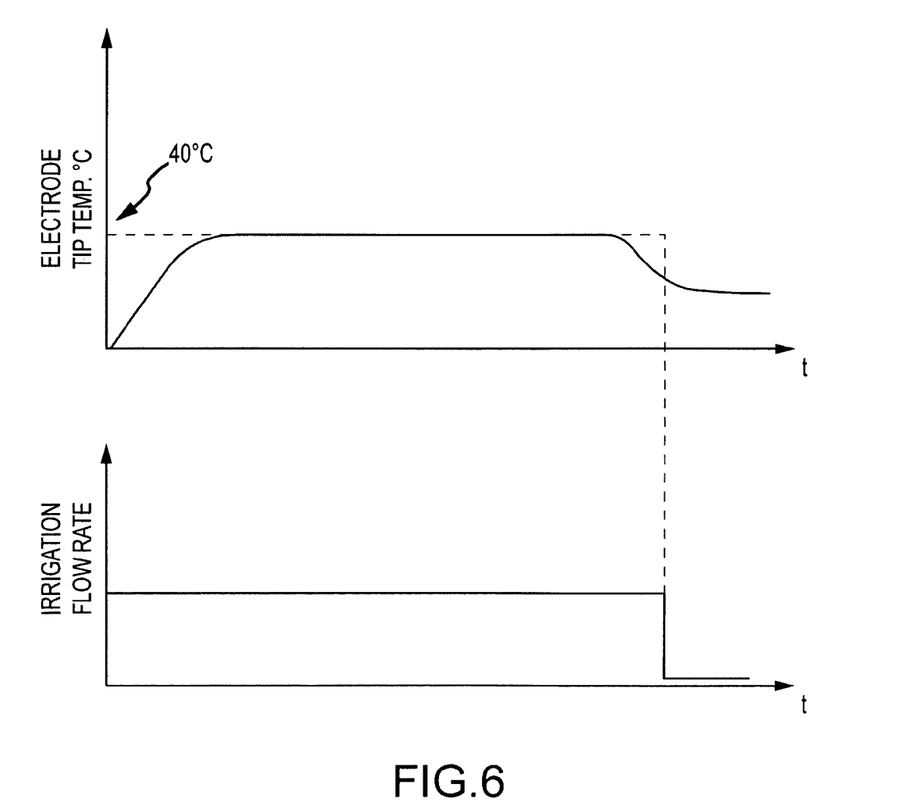
FIG. 6 is a graphical representation of a conventional tip electrode temperature response and irrigation flow according to the prior art.
Figure 7:
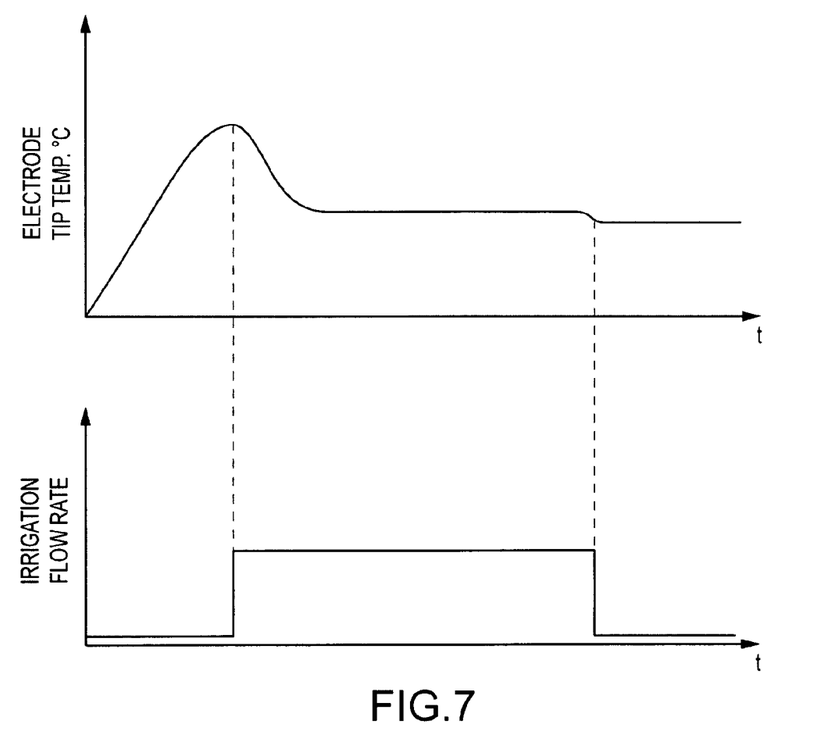
FIG. 7 is a graphical representation of the tip electrode temperature response and delayed irrigation flow rate according to an embodiment of the present invention.
Figure 8:
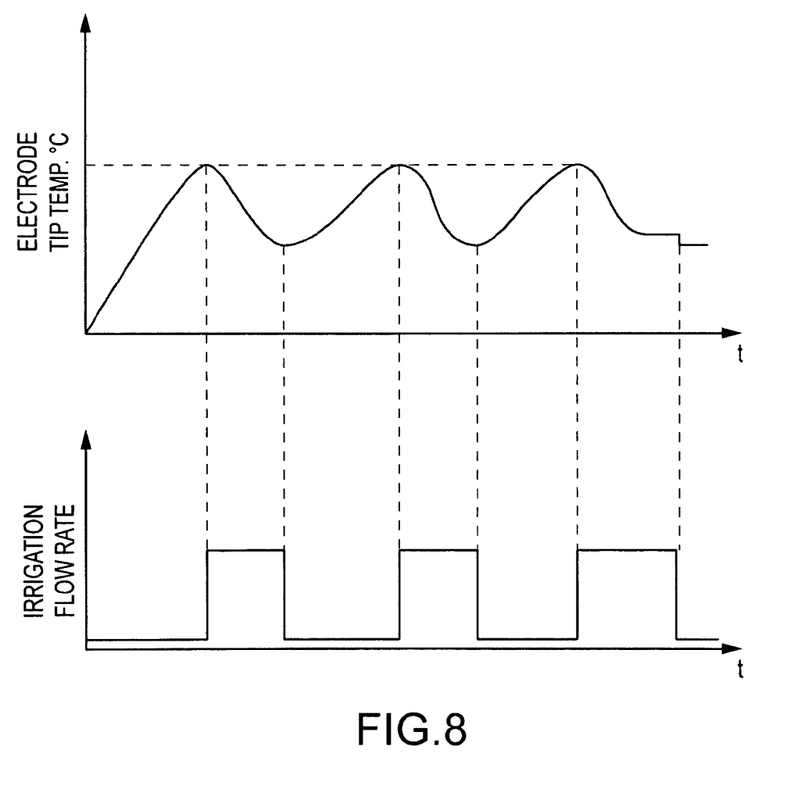
FIG. 8 is an graphical representation of the tip electrode temperature response and intermitted irrigation flow according to an embodiment of the present invention.

As represented in FIGS. 6-8, temperature readings of an electrode 10 of catheter assembly 12 and the provision of irrigation fluid have a direct correlation with one another. As generally shown in FIG. 6, the conventional method of introducing irrigation fluid upon the onset of the ablation procedure results in the electrode temperature only reaching approximately 40 degrees Celsius. However, this can result in less effective ablation with respect to a target area and there may be some regulation difficulties if the ablation electrode is in direct contact with the target tissue. In comparison, FIGS. 7 and 8, without limitation, illustrate delayed and intermitted irrigation, respectively, in accordance with embodiments of the present invention.

As generally shown in FIG. 7, irrigation fluid flow may initially be delayed following application of ablation energy. The delay in irrigation fluid flow may either be obtained through a fixed delay or a variable delay. The fixed delay may occur, for example, when irrigation flow is delayed for a fixed or predetermined period of time, such as, for example, 10-30 seconds after the start of the ablation energy. After a fixed period of time has passed, the irrigation fluid may be provided to the catheter assembly. In contrast, a variable delay may occur, for example, when irrigation flow is controlled by a predetermined temperature threshold. In a particular embodiment, the variable delay may occur and continue until a temperature threshold level, e.g., 65 degrees Celsius, is reached and then a constant irrigation fluid flow can be provided and maintained for the duration of the ablation procedure.

FIG. 8 illustrates an embodiment of an intermitted irrigation fluid flow and a correlation between irrigated fluid flow and resulting electrode temperature response. The intermitted irrigation flow may occur for either a fixed intermitted duration or for a variable intermitted duration. The fixed intermitted duration may, for example, occur for a predefined period of time, e.g., approximately 10-20 seconds, and then return back to a maintenance flow level (e.g., 2 cc/min). This flow control can occur for and throughout an entire ablation procedure. In other embodiments, a variable intermitted duration may be controlled by an upper predetermined electrode temperature threshold level (e.g., ranging from 50-70 degrees Celsius) and a lower predetermined electrode temperature threshold level (e.g., ranging from 37-45 degrees Celsius). Accordingly, only a maintenance irrigation flow level may be initially present (e.g., 2 cc/min), until an upper predetermined threshold level is reached and then irrigation fluid flow may be initiated. The irrigation fluid flow can be configured to continue until a lower predetermined electrode temperature threshold level is reached, at which point the irrigation fluid flow may be decreased to return to a maintenance flow level. The foregoing can continue in the form of a cycle or loop, which can result in an intermitted fluid flow throughout an entire ablation procedure. Alternately, the irrigation flow may be turned off periodically during the ablation procedure to check the temperature response of the electrode until the ablation is completed.

In accordance with the embodiments of the present invention, and performing ablation of biological tissue through the use of open irrigated catheter assemblies, a temperature threshold may be preset in connection with a generator 54. In embodiments, the temperature threshold level may range from 50-70 degrees Celsius, and for some embodiments may preferably be about 65 degrees Celsius. After a temperature threshold level is set or otherwise established, an open irrigated ablation catheter assembly 10 can be maneuvered to a target location (such as, for example, the surface of the heart). Once electrode 12 of catheter assembly 10 is provided at a desired target position, energy can be applied by generator 54 to electrode 10.

The present invention further provides a method of irrigating biological tissue. The method can be initiated by providing an irrigated catheter ablation system 50, 50'. The system 50, 50' can include an irrigated ablation catheter assembly, a fluid source connected to the catheter assembly, an energy source connected to the catheter assembly, and an irrigation temperature control mechanism in communication with the fluid source and energy source. The irrigated ablation catheter assembly 10 may be in accordance with teachings previously described. The method may include a step of establishing or presetting a temperature threshold for the system that regulates irrigation fluid flow from the passageway of the catheter assembly. The irrigated electrode of the irrigated ablation catheter assembly may be operatively positioned at a target location. Energy may then applied to the target location via an irrigated electrode. Temperature measurements associated with an electrode may be continuously collected. The temperature measurements can be continuously taken by a thermal sensor disposed within an irrigated electrode. After either a fixed period of time (fixed delay) or upon the temperature measurement reaching a temperature threshold level (variable delay), irrigation flow may be initiated or increased (if an original (e.g., maintenance flow was already present) to cool the electrode. Irrigation may continue until ablation is discontinued. As previously described, an application of fixed delay irrigation may cause the irrigation flow to be initiated, for example, about 10 to approximately 30 seconds after the application of the ablation energy was applied. In comparison, if variable delay irrigation is performed, the irrigation may be initiated after an upper temperature threshold level is reached, e.g., at about 50-70 degrees Celsius.

Another embodiment further includes a method of irrigating biological tissue involving an intermitted irrigation flow. In addition to the steps discussed above, additional temperature measurements of the irrigated electrode can be collected until a predetermined lower threshold is reached. Once a predetermined lower threshold level is reached, the irrigation flow may be discontinued. Temperatures can continued to be monitored and collected. If temperature measurements reach an upper temperature threshold level again, irrigation flow can be initiated or re-initiated, as the case may be. Such an intermitted irrigation cycle can continue until the ablation is formed. Alternately, the irrigation flow may be turned off periodically during the ablation procedure to check the temperature response of the electrode until the ablation is completed.

Although a number of embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An irrigated catheter ablation system comprising:
   an irrigated ablation catheter assembly including:
     an irrigated electrode having a proximal portion with a proximal end, a distal portion with a distal end, an outer body portion including an outer surface, an inner cavity defined within the outer body portion, and at least one passageway that extends from the inner cavity to the outer surface of the electrode, and
     a catheter shaft including a proximal end and a distal end;
   a fluid source connected to or in operative communication with the catheter assembly;
   an energy source connected to or in operative communication with the catheter assembly; and
   an irrigation temperature control mechanism in communication with the fluid source and the energy source,
   wherein the irrigation temperature control mechanism controls or regulates irrigation flow of fluid from the fluid source in response to temperature measurements received from a temperature sensor, wherein at least a portion of the temperature sensor is disposed within the outer body portion of the electrode,
   wherein the flow of fluid during ablation includes flow that alternates between a maintenance flow rate having a nonzero flow of fluid and an amplified flow rate having a flow of fluid that is greater than the maintenance flow rate, and
   wherein the energy source is configured to provide ablation energy for the electrode and wherein the irrigation flow of fluid includes a variable delay between the start of the provision of energy by the energy source and the initial start of the flow of fluid.

2. The system of claim 1, wherein the temperature sensor is positioned within the distal portion of the electrode.

3. The system of claim 1, wherein the irrigation temperature control mechanism is coupled to the energy source.

4. The system of claim 3, wherein the irrigation temperature control mechanism includes a controller.

5. The system of claim 1, wherein the fluid source includes a saline pump.

6. An irrigated catheter ablation system comprising:
   an irrigated ablation catheter assembly including:
     an irrigated electrode having a proximal portion with a proximal end, a distal portion with a distal end, an outer body portion including an outer surface, an inner cavity defined within the outer body portion, and at least one passageway that extends from the inner cavity to the outer surface of the electrode, and a catheter shaft including a proximal end and a distal end;
a fluid source connected to or in operative communication with the catheter assembly;
an energy source connected to or in operative communication with the catheter assembly; and
an irrigation temperature control mechanism in communication with the fluid source and the energy source,
wherein the irrigation temperature control mechanism controls or regulates irrigation flow of fluid from the fluid source in response to temperature measurements received from a temperature sensor, wherein at least a portion of the temperature sensor is disposed within the outer body portion of the electrode,
wherein the flow of fluid during ablation includes flow that alternates between a maintenance flow rate having a nonzero flow of fluid and an amplified flow rate having a flow of fluid that is greater than the maintenance flow rate, and
wherein the energy source is configured to provide ablation energy for the electrode and wherein the irrigation flow of fluid includes a fixed delay between the start of the provision of energy by the energy source and the initial start of the flow of fluid.

7. The system of claim 6, wherein the fixed delay ranges from about 10 seconds to about 30 seconds.

8. The system of claim 1, wherein the variable delay is controlled by an established or predetermined temperature threshold.

9. The system of claim 8, wherein the predetermined temperature threshold ranges from about 50 degrees Celsius to about 70 degrees Celsius.

10. The system of claim 1, wherein the irrigation flow of fluid is intermitted.

11. The system of claim 1, wherein at least one of said maintenance flow rate and said amplified flow rate occurs for a fixed duration.

12. The system of claim 11, wherein the fixed duration ranges from about 10 to about 20 seconds.

13. The system of claim 1, wherein at least one of said maintenance flow rate and said amplified flow rate occurs for a variable duration.

14. The system of claim 13, wherein the variable duration is controlled using an upper predetermined temperature threshold and a lower predetermined temperature threshold.

15. The system of claim 14, wherein the upper predetermined temperature threshold ranges from about 50 degrees Celsius to about 70 degrees Celsius.

16. The system of claim 14, wherein the lower predetermined temperature threshold ranges from about 37 degrees Celsius to about 45 degrees Celsius.

17. A method of irrigating biological tissue comprising:
providing an irrigated catheter ablation system including an irrigated ablation catheter assembly, a fluid source connected to the catheter assembly, an energy source connected to the catheter assembly, and an irrigation temperature control mechanism in communication with the fluid source and energy source, wherein the irrigated ablation catheter assembly includes a catheter shaft having a proximal end and a distal end, and an irrigated electrode having a proximal portion with a proximal end, a distal portion with a distal end, an outer body portion including an outer surface, an inner cavity defined within the outer body portion, and at least one passageway that extends from the inner cavity to the outer surface of the electrode;
presetting or establishing a temperature threshold for the irrigated catheter ablation system that regulates irrigation fluid flow from the passageway of the catheter assembly;
positioning the irrigated electrode of the irrigated ablation catheter assembly in operative range with respect to a target location;
applying energy from the energy source to the target location through the irrigated electrode;
obtaining or collecting temperature measurements from a thermal sensor disposed within the irrigated electrode;
irrigating the ablation electrode forming an irrigation flow through the passageway of the electrode; wherein the irrigation flow includes a delay between the applying energy step and an initial iteration of the irrigating step,
controlling the irrigation flow to include flow during the application of energy that alternates between a maintenance flow rate having a nonzero flow of fluid and an amplified flow rate having a flow of fluid that is greater than the maintenance flow rate; and
completing the application of energy to the target location to form at least a portion of an ablation lesion.

18. The method of claim 17, wherein the controlling step further includes:
irrigating the electrode at the amplified flow rate;
collecting the temperature measurements of the irrigated electrode until the measurements reach an established or predetermined lower temperature threshold;
reducing the irrigation flow through the passageway of the electrode to the maintenance flow rate;
collecting temperature measurements of the irrigated electrode until the measurements reach an established or predetermined upper temperature threshold;
increasing the irrigation flow through the passageway of the electrode to the amplified flow rate; and
repeating the sub-steps of collecting temperature measurements, reducing the irrigation flow rate, collecting temperature measurements, and increasing the flow rate until the ablation is complete.

19. The method of claim 17, wherein the delay is a fixed delay.

20. The method of claim 19, wherein the fixed delay ranges from about 10 seconds to about 30 seconds.

21. The method of claim 17, wherein the irrigation flow includes a variable delay between the applying energy step and an initial iteration of the irrigating step such that the irrigation is initiated when the electrode temperature reaches an upper temperature threshold.

22. The method of claim 21, wherein the upper temperature threshold ranges from about 50 degrees Celsius to about 70 degrees Celsius.

23. The method of claim 18, wherein the lower temperature threshold ranges from about 37 degrees Celsius to about 45 degrees Celsius.

* * * * *